United States Patent
Iwahara et al.

(10) Patent No.: US 6,825,386 B2
(45) Date of Patent: Nov. 30, 2004

(54) CATALYST FOR BISPHENOL COMPOUND PRODUCTION AND PROCESS FOR PRODUCING BISPHENOL COMPOUND WITH THE CATALYST

(75) Inventors: Masahiro Iwahara, Yamaguchi (JP); Tetsuya Saruwatari, Yamaguchi (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 10/468,152

(22) PCT Filed: Dec. 25, 2002

(86) PCT No.: PCT/JP02/13545

§ 371 (c)(1),
(2), (4) Date: Aug. 27, 2003

(87) PCT Pub. No.: WO03/055601

PCT Pub. Date: Jul. 10, 2003

(65) Prior Publication Data

US 2004/0127753 A1 Jul. 1, 2004

(30) Foreign Application Priority Data

Dec. 27, 2001 (JP) ........................................ 2001-395778

(51) Int. Cl.$^7$ .............................................. C07C 39/16
(52) U.S. Cl. .......................... 568/728; 521/32; 568/727
(58) Field of Search ................................. 568/728, 727; 521/32

(56) References Cited

U.S. PATENT DOCUMENTS

| | | | | |
|---|---|---|---|---|
| 3,394,089 A | * | 7/1968 | McNutt et al. | 521/33 |
| 3,634,341 A | * | 1/1972 | Gammill | 521/30 |
| 4,423,252 A | * | 12/1983 | Maki et al. | 568/728 |
| 6,429,343 B1 | | 8/2002 | Iwahara | |
| 6,586,637 B2 | | 7/2003 | Iwahara | |
| 6,653,513 B1 | | 11/2003 | Iwahara | |

FOREIGN PATENT DOCUMENTS

JP   11-246458   9/1999

* cited by examiner

Primary Examiner—Michael L. Shippen
(74) Attorney, Agent, or Firm—Oblon, Spivak, McClelland, Maier & Neustadt, P.C.

(57) ABSTRACT

Provided are a catalyst of high activity and good heavy substance resistance and alcohol resistance for production of bisphenols, and a method for producing bisphenols with the catalyst. The catalyst is a sulfonic acid-type cation-exchange resin modified with (a) a pyridinealkanethiol and (b) an aminoalkanethiol and/or a thiazolidine; and the method comprises reacting a phenol and a ketone in the presence of the catalyst for producing bisphenols.

7 Claims, No Drawings

CATALYST FOR BISPHENOL COMPOUND PRODUCTION AND PROCESS FOR PRODUCING BISPHENOL COMPOUND WITH THE CATALYST

BACKGROUND OF THE INVENTION

1. Field of the Invention

The present invention relates to a catalyst for production of bisphenols, and to a method for producing bisphenols with the catalyst, and more precisely, it relates to a catalyst of high activity and good heavy substance resistance and alcohol resistance for production of bisphenols, and to a method for producing bisphenols with the catalyst.

2. Description of the Related Art

It is known that bisphenol A [2,2-bis(4-hydroxyphenyl) propane] is an important compound for the starting material for engineering plastics such as polycarbonate resins and polyarylate resins and also for epoxy resins, and the demand for it is much increasing these days. It is publicly known that bisphenols such as bisphenol A are produced by reacting phenols and ketones in the presence of a catalyst, acid-type cation-exchange resin. For it, it is also known to modify the catalyst, acid-type cation-exchange resin with a nitrogen-containing sulfur compound for increasing the catalyst activity (e.g., JP-A 57-35533, 6-340563, 10-251179).

However, the modification with a nitrogen-containing sulfur compound has some drawbacks in that <1> if the degree of modification with it is high, the sulfonic acid points of the ion-exchange resin are damaged and the resin activity is thereby lowered and <2> if the degree of modification is high, heavy substances (side products in reaction) readily adhere to the pores of the ion-exchange resin to promote the resin degradation, but <3> if the degree of modification is low, alcohol in the starting material ketone promotes the resin degradation.

SUMMARY OF THE INVENTION

The present invention has been made in consideration of the viewpoint mentioned above, and it is to provide a catalyst of high activity and heavy substance resistance and alcohol resistance for production of bisphenols, and to provide a method for producing bisphenols with the catalyst.

We, the present inventors have assiduously studied and, as a result, have found that, when specific nitrogen-containing sulfur compounds are combined for the modifier for the catalyst, ion-exchange resin, then the object of the invention mentioned above can be effectively attained. On the basis of this finding, we have completed the present invention.

Specifically, the invention is.summarized as follows:

1. A catalyst for production of bisphenols, which is a sulfonic acid-type cation-exchange resin modified with (a) a pyridinealkanethiol and (b) an aminoalkanethiol and/or a thiazolidine.

2. The catalyst for production of bisphenols of above 1, in which from 8 to 55% of the sulfonic acid group is modified.

3. The catalyst for production of bisphenols of above 1 or 2, in which from 3 to 35% of the sulfonic acid group is modified with the component (a).

4. The catalyst for production of bisphenols of any of above 1 to 3, which is for producing bisphenol A.

5. A method for producing bisphenols, which comprises reacting a phenol and a ketone in the presence of the catalyst of any of above 1 to 4.

6. The method for producing bisphenols of above 5, wherein the phenol is unsubstituted phenol, the ketone is acetone and the bisphenol is bisphenol A.

7. The method for producing bisphenols of above 6, wherein the methanol content of acetone is at most 3,000 ppm.

DESCRIPTION OF THE PREFERRED EMBODIMENTS

The invention is described in detail hereinunder.

In its first aspect, the invention provides a catalyst for production of bisphenols, which is a sulfonic acid-type cation-exchange resin modified with (a) a pyridinealkanethiol (this may be referred to as a mercaptoalkylpyridine) and (b) an aminoalkanethiol (this may be referred to as a mercaptoalkylamine) and/or a thiazolidine.

In its second aspect, the invention provides a method for producing bisphenols, which comprises reacting a phenol and a ketone in the presence of the catalyst.

Of the sulfonic acid-type cation-exchange resin (hereinafter this may be abbreviated as ion-exchange resin), the matrix resin may be any of styrene-divinylbenzene copolymers, perfluoroethylene copolymers, phenol-formaldehyde polymers and others, but preferred are styrene-divinylbenzene copolymers. The resin may be gel or porous, but its degree of crosslinking is preferably low, for example, falling between 2 and 8%. The mean particle size of the ion-exchange resin may fall between 0.2 and 2.0 mm; and the particle size distribution uniformity may be broad, for example, falling between 1.0 and 1.6.

The modifier to modify the ion-exchange resin is a combination of the above-mentioned components (a) and (b).

The pyridinealkanethiol of the component (a) includes, for example, 2-mercaptomethylpyridine, 3-mercaptomethylpyridine, 2-mercaptoethylpyridine, 3-mercaptoethylpyridinne, 4-mercaptoethylpyridine and their hydrochlorides. Of those, preferred are 4-mercaptoethylpyridine and its hydrochloride.

The aminoalkanethiol of the component (b) includes, for example, 2-mercaptoethylamine, 3-mercaptopropylamine, 4-mercaptobutylamine and their hydrochlorides. Of those, preferred are 2-mercaptoethylamine and its hydrochloride.

The thiazolidine of the other component (b) includes, for example, 2,2-dimethylthiazolidine, 2-methyl-2-ethylthiazolidine, cycloalkylthiazolidine, 2-methyl-2-phenylthioazolidine, and 3-methylthioazolidine. Of those, preferred is 2,2-dimethylthiazolidine.

For modifying the ion-exchange resin, the modifier is dissolved in a solvent that dissolves it and is selected, for example, from water, alcohols and ethers, and the resulting solution is gradually (within a period of from 20 minutes to 1 hour) added to the non-modified ion-exchange resin that has been dispersed in the same solvent. For uniform reaction (for uniformly converting the sulfone group of the resin into a modified group), the system is preferably stirred. For further uniform reaction, the resin is modified in an aqueous solvent that contains acetic acid, monochloroaceic acid or trifluoroacetic acid.

For modifying the ion-exchange resin, the multiple components for the modifier may be applied to the resin all at a time or may be applied thereto one after another.

The reaction temperature may be room temperature or may be an elevated temperature (e.g., falling between 30 and 90° C.).

The amount of the modifier to be applied to the resin shall be so controlled that the degree of modification with the component (a) may fall between 3 and 35%, preferably between 5 and 30%, the degree of modification with the component (b) may fall between 5 and 52%, preferably between 5 and 30%, and the degree of total modification may fall between 8 and 55%, preferably between 10 and 45%.

In the second aspect of the invention, bisphenols are produced through reaction of phenols and ketones in the presence of the modified ion-exchange resin that serves as a catalyst.

Phenols must not have a para-positioned substituent relative to the hydroxyl group therein. Concretely, they are unsubstituted phenol; alkylphenols such as o-cresol, m-cresol, o-tert-butylphenol, 2,6-xylenol, 2,6-di-tert-butylphenol; and halogenophenols such as o-chlorophenol, m-chlorophenol, 2,6-dichlorophenol.

Concretely, ketones include acetone, methyl ethyl ketone, methyl isobutyl ketone, methyl n-propyl ketone, acetophenone, cyclohexanone; as well as aldehydes such as formalin, acetaldehyde, benzaldehyde.

The reaction mode is not specifically defined, but is preferably fixed-bed continuous reaction or batch reaction. For example, when the reaction is fixed-bed continuous reaction, its liquid hourly space velocity (LHSV) generally falls between 0.1 and 30 hr$^{-1}$, but preferably between 0.3 and 10 hr$^{-1}$.

The reaction condition is described. The ratio of phenol to ketone, phenol/ketone (by mol) generally falls between 3 and 30, but preferably between 5 and 15.

The reaction temperature generally falls between 50 and 150° C., but preferably between 60 and 110° C.

After the reaction, the non-reacted ketone, the produced water and the excess phenol are removed, and the resulting concentrate is cooled to 10 to 20° C. whereby the adduct of bisphenol-phenol (hereinafter referred to as phenol adduct) is deposited. Next, phenol is evaporated away from the phenol adduct under reduced pressure (falling between 100 and 700 Pa), and the residue is recrystallized from a suitable solvent to obtain the intended phenol product.

The method of the invention is favorable for production of bisphenol A from starting compounds of acetone and phenol.

Preferably, the alcohol content (in which methanol is at least 90% by mass) of acetone is at most 3,000 ppm, more preferably at most 2,000 ppm, as too much alcohol in the starting compound may degrade the catalyst.

EXAMPLES

The invention is described more concretely with reference to the following Examples, which, however, are not intended to restrict the scope of the invention.

Example 1

<1> Preparation of Catalyst

In a 1000-cc flask, 200 cc of an ion-exchange resin (Mitsubishi Chemical's trade name, Diaion SK-104—this was swollen with water) and 400 cc of methanol were stirred in suspension, to which was dropwise added a solution of 2.7 g of 4-mercaptoethylpyridine (this may be referred to as 4-pyridine-ethanethiol, and will be hereinunder abbreviated as PET) in 50 cc of methanol within a period of 30 minutes. After the addition, this was stirred for 1 hour, and then the ion-exchange resin was taken out through filtration, and washed twice with 100 cc of ion-exchanged water. A part of the thus-separated ion-exchange resin was dried, and analyzed for acidity through titration. As a result, 8% of the acid points of the resin were modified (neutralized) with PET. Next, in a 1000-cc flask, the PET-modified resin and 400 cc of ion-exchanged water were stirred in suspension, to which was dropwise added a solution of 2.0 g of 2,2-dimethylthiazolidine (hereinafter this will be abbreviated as DMT) in 50 cc of ion-exchanged water within a period of 30 minutes. After the addition, this was stirred for 1 hour, and then the ion-exchange resin was taken out through filtration, and washed twice with 100 cc of ion-exchanged water. A part of the thus-separated ion-exchange resin was dried, and analyzed for acidity through titration. 15% of the acid points of the resin were modified (neutralized). This means that the degree of modification with DMT is 7%.

<2> Reaction 69 cc of the PET/DMT-modified ion-exchange resin (swollen with water) was filled in a stainless column, in which acetone was reacted with phenol. The reaction temperature was 75° C.; and LHSV was 6 hr$^{-1}$ (the acetone flow was 15 cc/hr, the methanol content of acetone was 300 pp, and the phenol flow was 277 cc/hr). The reaction result was as follows: Just after the start of the reaction, the phenol conversion was 10.3%. 400 hours after the start of the reaction, the phenol conversion was 8.6%. Accordingly, the phenol conversion reduction rate was 1.7%/400 hr.

Comparative Example 1

<1> Preparation of Catalyst

In the same manner as in Example 1, the ion-exchange resin was modified with PET alone. The degree of modification of the resin was 8%.

<2> Reaction 69 cc of the PET -modified ion-exchange resin (swollen with water) was filled in a stainless column, in which acetone was reacted with phenol under the same condition as in Example 1. The reaction result was as follows: Just after the start of the reaction, the phenol conversion was 9.5%. 400 hours after the start of the reaction, the phenol conversion was 5.4%. Accordingly, the phenol conversion reduction rate was 4.1%/400 hr.

Comparative Example 2

<1> Preparation of Catalyst

In the same manner as in Example 1, the ion-exchange resin was modified with DMT alone. The degree of modification of the resin was 7%.

<2> Reaction 69 cc of the DMT-modified ion-exchange resin (swollen with water) was filled in a stainless column, in which acetone was reacted with phenol under the same condition as in Example 1. The reaction result was as follows: Just after the start of the reaction, the phenol conversion was 7.9%. 400 hours after the start of the reaction, the phenol conversion was 5.7% Accordingly, the phenol conversion reduction rate was 2.2%/400 hr.

Comparative Example 3
<1> Preparation of Catalyst
50 cc of the PET-modified ion-exchange resin (swollen with water) that had been prepared in Comparative Example 1 and 50 cc of the DMT-modified ion-exchange resin (swollen with water) that had been prepared in Comparative Example 2 were suspended in 200 cc of ion-exchanged water, and stirred for 20 minutes.
<2> Reaction
69 cc of the mixture of the PET-modified ion-exchange resin (swollen with water) and the DMT-modified ion-exchange resin (swollen with water) was filled in a stainless column, in which acetone was reacted with phenol under the same condition as in Example 1. The reaction result was as follows: Just after the start of the reaction, the phenol conversion was 8.8%. 400 hours after the start of the reaction, the phenol conversion was 5.3%. Accordingly, the phenol conversion reduction rate was 3.5%/400 hr.

Example 2
<1> Preparation of Catalyst
In a 1000-cc flask, 200 cc of an ion-exchange resin (Mitsubishi Chemical's trade name, Diaion SK-104—this was swollen with water) and 400 cc of ion-exchanged water were stirred in suspension, to which was dropwise added a solution of 1.8 g of 2-mercaptoethylamine (this may be referred to as 2-aminoethanethiol, and will be hereinafter referred to as AET) in 50 cc of in-exchanged water within a period of 30 minutes. After the addition, this was stirred for 1 hour, and then the ion-exchange resin was taken out through filtration, and washed twice with 100 cc of ion-exchanged water. A part of the thus-separated ion-exchange resin was dried, and analyzed for acidity through titration. As a result, 10% of the acid points of the resin were modified with AET. Next, in a 1000-cc flask, the AET-modified resin and 400 cc of methanol were stirred in suspension, to which was dropwise added a solution of 5.0 g of PET in 50 cc of methanol within a period of 30 minutes. After the addition, this was stirred for 1 hour, and then the ion-exchange resin was taken out through filtration, and washed twice with 100 cc of ion-exchanged water. A part of the thus-separated ion-exchange resin was dried, and analyzed for acidity through titration. 25% of the acid points of the resin were modified. This means that the degree of modification with PET is 15%.
<2> Reaction
69 cc of the AET/PET-modified ion-exchange resin (swollen with water) was filled in a stainless column, in which acetone was reacted with phenol. The reaction temperature was 75° C.; and LHSV was 6 hr$^{-1}$ (the acetone flow was 15 cc/hr, the methanol content of acetone was 1000 ppm, and the phenol flow was 277 cc/hr). The reaction result was as follows: Just after the start of the reaction, the phenol conversion was 11.7%. 400 hours after the start of the reaction, the phenol conversion was 10.1%. Accordingly, the phenol conversion reduction rate was 1.6%/400 hr.

Comparative Example 4
<1> Preparation of Catalyst
In the same manner as in Example 2, the ion-exchange resin was modified with AET alone. The degree of modification of the resin was 10%.
<2> Reaction
69 cc of the AET-modified ion-exchange resin (swollen with water) was filled in a stainless column, in which acetone was reacted with phenol under the same condition as in Example 2. The reaction result was as follows: Just after the start of the reaction, the phenol conversion was 8.2%. 400 hours after the start of the reaction, the phenol conversion was 5.8%. Accordingly, the phenol conversion reduction rate was 2.4%/400 hr.

Comparative Example 5
<1> Preparation of Catalyst
In the same manner as in Example 2, the ion-exchange resin was modified with PET alone. The degree of modification of the resin was 15%.
<2> Reaction
69 cc of the PET-modified ion-exchange resin (swollen with water) was filled in a stainless column, in which acetone was reacted with phenol under the same condition as in Example 2. The reaction result was as follows: Just after the start of the reaction, the phenol conversion was 11.6%. 400 hours after the start of the reaction, the phenol conversion was 7.4%. Accordingly, the phenol conversion reduction rate was 4.2%/400 hr.

Comparative Example 6
<1> Preparation of Catalyst
50 cc of the AET-modified ion-exchange resin (swollen with water) that had been prepared in Comparative Example 4 and 50 cc of the PET-modified ion-exchange resin (swollen with water) that had been prepared in Comparative Example 5 were suspended in 200 cc of ion-exchanged water, and stirred for 20 minutes.
<2> Reaction
69 cc of the mixture of the AET-modified ion-exchange resin (swollen with water) and the PET-modified ion-exchange resin (swollen with water) was filled in a stainless column, in which acetone was reacted with phenol under the same condition as in Example 2. The reaction result was as follows: Just after the start of the reaction, the phenol conversion was 10.1%. 400 hours after the start of the reaction, the phenol conversion was 7.0%. Accordingly, the phenol conversion reduction rate was 3.1%/400 hr.

Example 3
<1> Preparation of Catalyst
In a 1000-cc flask, 200 cc of an ion-exchange resin (Mitsubishi Chemical's trade name, Diaion SK-104—this was swollen with water) and 400 cc of methanol were stirred in suspension, to which were dropwise added a solution of 6.6 g of PET in 50 cc of methanol and a solution of 5.6 g of DMT in 50 cc of methanol within a period of 60 minutes. After the addition, this was stirred for 1 hour, and then the ion-exchange resin was taken out through filtration, and washed twice with 100 cc of ion-exchanged water. A part of the thus-separated ion-exchange resin was dried, and analyzed for acidity through titration. The resin were modified with PET by 20% and with DMT by 20%.

<2> Reaction 69 cc of the PET/DMT-modified ion-exchange resin (swollen with water) was filled in a stainless column, in which acetone was reacted with phenol. The reaction temperature was 75° C.; and LHSV was 6 hr$^{-1}$ (the acetone flow was 15 cc/hr, the methanol content of acetone was 2800 ppm, and the phenol flow was 277 cc/hr). The reaction result was as follows: Just after the start of. the reaction, the phenol conversion was 11.0%. 400 hours after the start of the reaction, the phenol conversion was 9.0%. Accordingly, the phenol conversion reduction. rate was 2.0%/400 hr.

Comparative Example 7

<1> Preparation of Catalyst

In the same manner as in Example 3, the ion-exchange resin was modified with PET alone. The degree of modification of the resin was 20%.

<2> Reaction 69 cc of the PET-modified ion-exchange resin (swollen with water) was filled in a stainless column, in which acetone was reacted with phenol under the same condition as in Example 3. The reaction result was as follows: Just after the start of the reaction, the phenol conversion was 12.0%. 400 hours after the start of the reaction, the phenol conversion was 5.6% Accordingly, the phenol conversion reduction rate was 6.4%/400 hr.

Comparative Example 8

<1> Preparation of Catalyst

In the same manner as in Example 3, the ion-exchange resin was modified with DMT alone. The degree of modification of the resin was 20%.

<2> Reaction 69 cc of the DMT-modified ion-exchange resin (swollen with water) was filled in a stainless column, in which acetone was reacted with phenol under the same condition as in Example 3. The reaction result was as follows: Just after the start of the reaction, the phenol conversion was 8.8%. 400 hours after the start of the reaction, the phenol conversion was 5.0%. Accordingly, the phenol conversion reduction rate was 3.8%/400 hr.

Comparative Example 9

<1> Preparation of Catalyst 50 cc of the PET-modified ion-exchange resin (swollen with water) that had been prepared in Comparative Example 7 and 50 cc of the DMT-modified ion-exchange resin (swollen with water) that had been prepared in Comparative Example 8 were suspended in 200 cc of ion-exchanged water, and stirred for 20 minutes.

<2> Reaction 69 cc of the mixture of the PET-modified ion-exchange resin (swollen with water) and the DMT-modified ion-exchange resin (swollen with water) was filled in a stainless column, in which acetone was reacted with phenol under the same condition as in Example 3. The reaction result was as follows: Just after the start of the reaction, the phenol conversion was 10.2%. 400 hours after the start of the reaction, the phenol conversion was 6.0%. Accordingly, the phenol conversion reduction rate was 4.2%/400 hr.

Example 4

<1> Preparation of Catalyst

In a 1000-cc flask, 200 cc of an ion-exchange resin (Mitsubishi Chemical's trade name, Diaion SK-104—this was swollen with water) and 400 cc of methanol were stirred in suspension, to which was dropwise added a solution of 9.9 g PET in 100 cc of methanol within a period of 30 minutes. After the addition, this was stirred for 1 hour, and then the ion-exchange resin was taken out through filtration, and washed twice with 100 cc of ion-exchanged water. A part of the thus-separated ion-exchange resin was dried, and analyzed for acidity through titration. As a result, 30% of the acid points of the resin were modified with PET. Next, in a 1000-cc flask, the PET-modified resin and 400 cc of ion-exchanged water were stirred in suspension, to which was dropwise added a solution of 2.8 g of DMT in 50 cc of ion-exchanged water within a period of 30 minutes. After the addition, this was stirred for 1 hour, and then the ion-exchange resin was taken out through filtration, and washed twice with 100 cc of ion-exchanged water. A part of the thus-separated ion-exchange resin was dried, and analyzed for acidity through titration. 40% of the acid points of the resin were modified. This means that the degree of modification with DMT is 10%.

<2> Reaction 69 cc of the PET/DMT-modified ion-exchange resin (swollen with water) was filled in a stainless column, in which acetone was reacted with phenol. The reaction temperature was 75° C.; and LHSV was 6 hr$^{-1}$ (the acetone flow was 15 cc/hr, the methanol content of acetone was 2000 ppm, and the phenol flow was 277 cc/hr). The reaction result was as follows: Just after the start of the reaction, the phenol conversion was 10.8%. 400 hours after the start of the reaction, the phenol conversion was 8.7%. Accordingly, the phenol conversion reduction rate was 2.1%/400 hr.

Comparative Example 10

<1> Preparation of Catalyst

In the same manner as in Example 4, the ion-exchange resin was modified with PET alone. The degree of modification of the resin was 30%.

<2> Reaction 69 cc of the PET -modified ion-exchange resin (swollen with water) was filled in a stainless column, in which acetone was reacted with phenol under the same condition as in Example 4. The reaction result was as follows: Just after the start of the reaction, the phenol conversion was 11.8%. 400 hours after the start of the reaction, the phenol conversion was 6.6%. Accordingly, the phenol conversion reduction rate was 5.2%/400 hr.

Comparative Example 11

<1> Preparation of Catalyst

In the same manner as in Example 4, the ion-exchange resin was modified with DMT alone. The degree of modification of the resin was 10%.

<2> Reaction 69 cc of the DMT-modified ion-exchange resin (swollen with water) was filled in a stainless column, in which acetone was reacted with phenol under the same condition as in Example 4. The reaction result was as follows: Just after the start of the reaction, the phenol conversion was 8.7%.

400 hours after the start of the reaction, the phenol conversion was 4.3%. Accordingly, the phenol conversion reduction rate was 4.4%/400 hr.

Comparative Example 12

<1> Preparation of Catalyst 50 cc of the PET-modified ion-exchange resin (swollen with water) that had been prepared in Comparative Example 10 and 50 cc of the DMT-modified ion-exchange resin (swollen with water) that had been prepared in Comparative Example 11 were suspended in 200 cc of ion-exchanged water, and stirred for 20 minutes.

<2> Reaction 69 cc of the mixture of the PET-modified ion-exchange resin (swollen with water) and the DMT-modified ion-exchange resin (swollen with water) was filled in a stainless column, in which acetone was reacted with phenol under the same condition as in Example 4. The reaction result was as follows: Just after the start of the reaction, the phenol conversion was 10.0%. 400 hours after the start of the reaction, the phenol conversion was 5.2%. Accordingly, the phenol conversion reduction rate was 4.8%/400 hr.

Example 5

<1> Preparation of Catalyst

In a 1000-cc flask, 200 cc of an ion-exchange resin (Mitsubishi Chemical's trade name, Diaion SK-104—this was swollen with water) and 400 cc of methanol were stirred in suspension, to which was dropwise added a solution of 3.3 g PET in 50 cc of methanol within a period of 30 minutes. After the addition, this was stirred for 1 hour, and then the ion-exchange resin was taken out through filtration, and washed twice with 100 cc of ion-exchanged water. A part of the thus-separated ion-exchange resin was dried, and analyzed for acidity through titration. As a result, 10% of the acid points of the resin were modified with PET. Next, in a 1000-cc flask, the PET-modified resin and 400 cc of ion-exchanged water were stirred in suspension, to which was dropwise added a solution of 2.8 g of AET in 50 cc of ion-exchanged water within a period of 30 minutes. After the addition, this was stirred for 1 hour, and then the ion-exchange resin was taken out through filtration, and washed twice with 100 cc of ion-exchanged water. A part of the thus-separated ion-exchange resin was dried, and analyzed for acidity through titration. 25% of the acid points of the resin were modified. This means that the degree of modification with AET is 15%. Next, the PET/AET-modified resin and 400 cc of ion-exchanged water were stirred in suspension in a 1000-cc flask, to which was added a solution of 4.2 g of DMT in 50 cc of ion-exchanged water within a period of 30 minutes. After the addition, this was stirred for 1 hour, and then the ion-exchange resin was taken out through filtration, and washed twice with 100 cc of ion-exchanged water. A part of the thus-separated ion-exchange resin was dried, and analyzed for acidity through titration. 40% of the acid points of the resin were modified. This means that the degree of modification with DMT is 15%.

<2> Reaction 69 cc of the PET/AET/DMT-modified ion-exchange resin (swollen with water) was filled in a stainless column, in which acetone was reacted with phenol. The reaction temperature was 75° C.; and LHSV was 6 hr$^{-1}$ (the acetone flow was 15 cc/hr, the methanol content of acetone was 800 ppm, and the phenol flow was 277 cc/hr). The reaction result was as follows: Just after the start of the reaction, the phenol conversion was 10.2%. 400 hours after the start of the reaction, the phenol conversion was 8.8%. Accordingly, the phenol conversion reduction rate was 1.4%/400 hr.

Comparative Example 13

<1> Preparation of Catalyst

In the same manner as in Example 5, the ion-exchange resin was modified with PET alone. The degree of modification of the resin was 10%.

<2> Reaction 69 cc of the PET -modified ion-exchange resin (swollen with water) was filled in a stainless column, in which acetone was reacted with phenol under the same condition as in Example 5. The reaction result was as follows: Just after the start of the reaction, the phenol conversion was 9.8%. 400 hours after the start of the reaction, the phenol conversion was 5.5.%. Accordingly, the phenol conversion reduction rate was 4.3%/400 hr.

Comparative Example 14

<1> Preparation of Catalyst

In a 1000-cc flask, 200 cc of an ion-exchange resin (Mitsubishi Chemical's trade name, Diaion SK-104—this was swollen with water) and 400 cc of ion-exchanged water were stirred in suspension, to which was dropwise added a solution of 2.8 g AET in 50 cc of ion-exchanged water within a period of 30 minutes. After the addition, this was stirred for 1 hour, and then the ion-exchange resin was taken out through filtration, and washed twice with 100 cc of ion-exchanged water. A part of the thus-separated ion-exchange resin was dried, and analyzed for acidity through titration. As a result, 15% of the acid points of the resin were modified with AET. Next, in a 1000-cc flask, the AET-modified resin and 400 cc of ion-exchanged water were stirred in suspension, to which was dropwise added a solution of 4.2 g of DMT in 50 cc of ion-exchanged water within a period of 30 minutes. After the addition, this was stirred for 1 hour, and then the ion-exchange resin was taken out through filtration, and washed twice with 100 cc of ion-exchanged water. A part of the thus-separated ion-exchange resin was dried, and analyzed for acidity through titration. 30% of the acid points of the resin were modified. This means that the degree of modification with DMT is 15%.

<2> Reaction 69 cc of the AET/DMT-modified ion-exchange resin (swollen with water) was filled in a stainless column, in which acetone was reacted with phenol under the same condition as in Example 5. The reaction result was as follows: Just after the start of the reaction, the phenol conversion was 8.3%. 400 hours after the start of the reaction, the phenol conversion was 5.8%. Accordingly, the phenol conversion reduction rate was 2.5%/400 hr.

Comparative Example 15

<1> Preparation of Catalyst

In the same manner as in Comparative Example 14, the ion-exchange resin was modified with AET alone to prepare an AET-modified ion-exchange resin. The degree of modification of the resin was 15%. Also in the same manner as in Comparative Example 14, the ion-exchange resin was modified with DMT alone to prepare a DMT-modified ion-exchange resin. The degree of modification of the resin was 15%. 50 cc of the PET-modified ion-exchange resin (swollen with water) that had been prepared in Comparative Example 13, 25 cc of the above AET-modified ion-exchange resin (swollen with water), and 25 cc of the above DMT-modified ion-exchange resin (swollen with water) were suspended in 200 cc of ion-exchanged water, and stirred for 20 minutes.

<2> Reaction 69 cc of the mixture of the PET-modified ion-exchange resin (swollen with water), the AET-modified ion-exchange resin (swollen with water) and the DMT-modified ion-exchange resin (swollen with water) was filled in a stainless column, in which acetone was reacted with phenol under the same condition as in Example 5. The reaction result was as follows: Just after the start of the reaction, the phenol conversion was 8.8%. 400 hours after the start of the reaction, the phenol conversion was 5.0%. Accordingly, the phenol conversion reduction rate was 3.8%/400 hr.

The catalysts prepared in the above are summarized in Table 1; and the test results obtained in the above are in Table 2.

TABLE 1

| | Modifier (degree of modification) | | Catalyst |
|---|---|---|---|
| | Component (a) | Component (b) | Morphology |
| Example 1 | PET (8%) | DMT (7%) | binary system |
| Comp. Ex. 1 | PET (8%) | — | single |
| Comp. Ex. 2 | — | DMT (7%) | single |
| Comp. Ex. 3 | PET (8%) | DMT (7%) | mixed system |
| Example 2 | PET (15%) | AET (10%) | binary system |
| Comp. Ex. 4 | — | AET (10%) | single |
| Comp. Ex. 5 | PET (15%) | — | single |
| Comp. Ex. 6 | PET (15%) | AET (10%) | mixed system |
| Example 3 | PET (20%) | DMT (20%) | binary system |
| Comp. Ex. 7 | PET (20%) | — | single |
| Comp. Ex. 8 | — | DMT (20%) | single |
| Comp. Ex. 9 | PET (20%) | DMT (20%) | mixed system |
| Example 4 | PET (30%) | DMT (10%) | binary system |
| Comp. Ex. 10 | PET (30%) | — | single |
| Comp. Ex. 11 | — | DMT (10%) | single |
| Comp. Ex. 12 | PET (30%) | DMT (10%) | mixed system |
| Example 5 | PET (10%) | AET (15%) DMT (15%) | ternary system |
| Comp. Ex. 13 | PET (10%) | — | single |
| Comp. Ex. 14 | — | AET (15%) DMT (15%) | binary system |
| Comp. Ex. 15 | PET (10%) | AET (15%) DMT (15%) | mixed system |

Note)
PET: 4-pyridine-ethanethiol
DMT: 2,2-dimethylthiazolidine
AET: 2-aminoethanethiol

TABLE 2

| | Methanol* (ppm) | Initial Conversion (%) | Conversion after 400 hrs (%) | Conversion Reduction Rate (%) per 400 hrs |
|---|---|---|---|---|
| Example 1 | 300 | 10.3 | 8.6 | 1.7 |
| Comp. Ex. 1 | 300 | 9.5 | 5.4 | 4.1 |
| Comp. Ex. 2 | 300 | 7.9 | 5.7 | 2.2 |
| Comp. Ex. 3 | 300 | 8.8 | 5.3 | 3.3 |
| Example 2 | 1000 | 11.7 | 10.1 | 1.6 |
| Comp. Ex. 4 | 1000 | 8.2 | 5.8 | 2.4 |
| Comp. Ex. 5 | 1000 | 11.6 | 7.4 | 4.2 |
| Comp. Ex. 6 | 1000 | 10.1 | 7.0 | 3.1 |
| Example 3 | 2800 | 11.0 | 9.0 | 2.0 |
| Comp. Ex. 7 | 2800 | 12.0 | 5.6 | 6.4 |
| Comp. Ex. 8 | 2800 | 8.8 | 5.0 | 3.8 |
| Comp. Ex. 9 | 2800 | 10.2 | 6.0 | 4.2 |
| Example 4 | 2000 | 10.8 | 8.7 | 2.1 |
| Comp. Ex. 10 | 2000 | 11.8 | 6.6 | 5.2 |
| Comp. Ex. 11 | 2000 | 8.7 | 4.4 | 4.3 |
| Comp. Ex. 12 | 2000 | 10.0 | 5.2 | 4.8 |
| Example 5 | 800 | 10.2 | 8.8 | 1.4 |
| Comp. Ex. 13 | 800 | 9.8 | 5.5 | 4.3 |
| Comp. Ex. 14 | 800 | 8.3 | 5.8 | 2.5 |
| Comp. Ex. 15 | 800 | 8.8 | 5.0 | 3.8 |

Note) *This indicates the methanol content of acetone.

As described in detail hereinabove with reference to its preferred embodiments, the invention provides a catalyst of high activity and good heavy substance resistance and alcohol resistance for production of bisphenols, and to a method for producing bisphenols with the catalyst.

What is claimed is:

1. A catalyst for producing bisphenols, comprising a sulfonic acid-type cation-exchange resin modified with (a) a pyridinealkanethiol and (b) an aminoalkanethiol and/or a thiazolidine.

2. The catalyst for producing bisphenols as claimed in claim 1, wherein from 8 to 55% of the sulfonic acid group is modified.

3. The catalyst for producing bisphenols as claimed in claim 1, wherein from 3 to 35% of the sulfonic acid group is modified with the component (a).

4. A catalyst for producing bisphenol A comprising the catalyst as claimed in claim 1.

5. A method for producing bisphenols, comprising reacting a phenol and a ketone in the presence of the catalyst of claim 1.

6. The method for producing bisphenols as claimed in claim 5, wherein the phenol is unsubstituted phenol, the ketone is acetone and the bisphenol is bisphenol A.

7. The method for producing bisphenols as claimed in claim 6, wherein the acetone has a methanol content of at most 3,000 ppm.

* * * * *